United States Patent [19]

Shiono et al.

[11] Patent Number: 4,799,166

[45] Date of Patent: Jan. 17, 1989

[54] APPARATUS FOR AUTOMATICALLY ANALYZING GASES IN OIL

[75] Inventors: Katsumi Shiono; Hideo Shinohara; Sadao Naito; Goroo Ikeda, all of Ako, Japan

[73] Assignee: Mitsubishi Denki Kabushiki Kaisha, Japan

[21] Appl. No.: 166,722

[22] Filed: Mar. 2, 1988

Related U.S. Application Data

[63] Continuation of Ser. No. 856,472, Apr. 28, 1986, abandoned.

[51] Int. Cl.⁴ .............................................. H02H 7/04
[52] U.S. Cl. ...................................... 364/497; 361/35; 361/37
[58] Field of Search ...................... 364/497; 361/35, 37

[56] References Cited

U.S. PATENT DOCUMENTS

| | | | |
|---|---|---|---|
| 3,680,359 | 8/1972 | Lynch | 361/37 X |
| 4,229,968 | 10/1980 | Muldoon | 364/497 X |
| 4,354,242 | 10/1982 | Geanster et al. | 364/501 X |
| 4,357,300 | 11/1982 | Nicklaus | 364/497 X |
| 4,471,348 | 9/1984 | London et al. | 364/551 X |
| 4,524,420 | 6/1985 | Glodo et al. | 364/497 |
| 4,654,806 | 3/1987 | Poyser | 361/35 |

FOREIGN PATENT DOCUMENTS

| | | | |
|---|---|---|---|
| 52-2490 | 1/1977 | Japan | 364/497 |
| 58-193464 | 11/1983 | Japan | 364/497 |

Primary Examiner—R. R. Kucia
Attorney, Agent, or Firm—Leydig, Voit & Mayer

[57] ABSTRACT

An apparatus for automatically analyzing gases in oil, wherein a gas analyzer analyzes the total quantity of combustible gases extracted from the oil or the quantities of several specified ones of the combustible gases, comprising a data processor determining the presence or absence of the abnormality of an oil-immersed equipment on the basis of the increasing or decreasing trend of the analyzed results obtained in several analyzing operations, or calculating the sampling period of oil sampling and analytical processing routines, on the basis of the increasing or decreasing trend of the analyzed results, whereby the abnormality can be automatically determined with a high reliability.

1 Claim, 4 Drawing Sheets

APPARATUS FOR AUTOMATICALLY ANALYZING GASES IN OIL

This application is a continuation of application Ser. No. 856,472, filed Apr. 28, 1986, now abandoned.

BACKGROUND OF THE INVENTION

This invention relates to an apparatus for automatically analyzing and data processing combustible gases dissolved in the insulating oil of oil-immersed equipment, for example, oil-immersed transformers. More particularly, it relates to an apparatus for automatically analyzing gases in oil which is provided with a function for determining whether there is an abnormality in oil-immersed equipment based on the increasing trend or decreasing trend of the analyzed results of the quantities of combustible gases and a function for automatically changing the sampling period of oil sampling and analytical processing routines.

When an abnormality such as arc discharge, corona discharge or local heating has taken place in an oil-immersed equipment, an electrical insulating material, for example, insulating oil or insulating paper near an abnormal part is decomposed to produce combustible gases. The majority of the produced combustible gases are dissolved in the insulating oil. Therefore, the combustible gases in the oil have hitherto been analyzed in order to find out the abnormality in the oil-immersed equipment at an early stage and to prevent any accident from occurring. As apparatuses for detecting the combustible gases in the oil, the mainstream has heretofore been formed by off-line processing routine wherein a man samples the oil from the oil-immersed equipment and then analyzes the sampled oil with an analyzer such a gas chromatograph. In recent years, an automatic analyzing apparatus of on-line processing routine, which is connected to a transformer by a pipe or two pipes and which automatically performs steps from oil sampling to analysis, has also become commercially available.

The analyzing apparatus of both types can detect the absolute values of the quantities of the combustible gases in the oil. However, neither of them can execute the determination processing of an increasing trend or decreasing trend of the analyzed results of the combustible gas quantities in the oil, the determination processing of the trend being another important factor, for detecting early the abnormality in oil-immersed equipment, and a man has always observed the trend and determined the presence or absence of the abnormality. As illustrated in FIG. 1, with the method of foreknowing the abnormality on the basis of only the absolute values of the combustible gas quantities in the oil, the abnormality is found out at a point of time $t_2$. In contrast, the method of foreknowing the abnormality in the oil-immersed equipment on the basis of the increasing trend of the analyzed results makes it possible to find out the abnormality at a point of time $t_1$ before the point of time $t_2$. Therefore, the latter method is an effective measure with which the abnormality can be found out earlier than with the former method. The prior art, however, has had the disadvantages that labor for collecting and processing data is required and that skills are required for detecting the trends and for determining the presence or absence of the abnormality. Another disadvantage is that, if the result of determination by a man as stated above is "requiring attention", much labor is expended in shortening the sampling period of oil sampling and analytical processing routines in order to render a more precise determination.

SUMMARY OF THE INVENTION

This invention has been made in order to eliminate the disadvantages of the prior-art apparatus for analyzing combustible gases in oil as mentioned above, and has for its object to provide an apparatus for automatically analyzing gases in oil provided with a function according to which variation with time of the quantities of combustible gases in the oil is found on the basis of the gas quantities automatically analyzed, whereupon the abnormality in oil-immersed equipment is determined on the basis of an increasing trend or decreasing trend of the analyzed results.

Another object of this invention is to provide an apparatus for automatically analyzing gases in oil provided with a function according to which the sampling period of oil sampling and analytical processing routines is automatically changed on the basis of the increasing trend or decreasing trend of analyzed results.

This invention accordingly consists in an apparatus for automatically analyzing gases in oil comprising a gas extractor for deriving extract combustible gases contained in the oil, a gas analyzer for deriving the combustible gases extracted by the gas extractor to analyze a total quantity of the combustible gases or quantities of specified ones of the combustible gases, and a data processor for storing results analyzed by said gas analyzer, for finding a variation with time of the analyzed results and for outputting data necessary to monitor the oil-immersed equipment on the basis of the analyzed results.

DESCRIPTION OF THE PREFERRED EMBODIMENTS

Now, this invention will be described in detail in conjunction with embodiments shown in the accompanying drawings.

Figure 1:
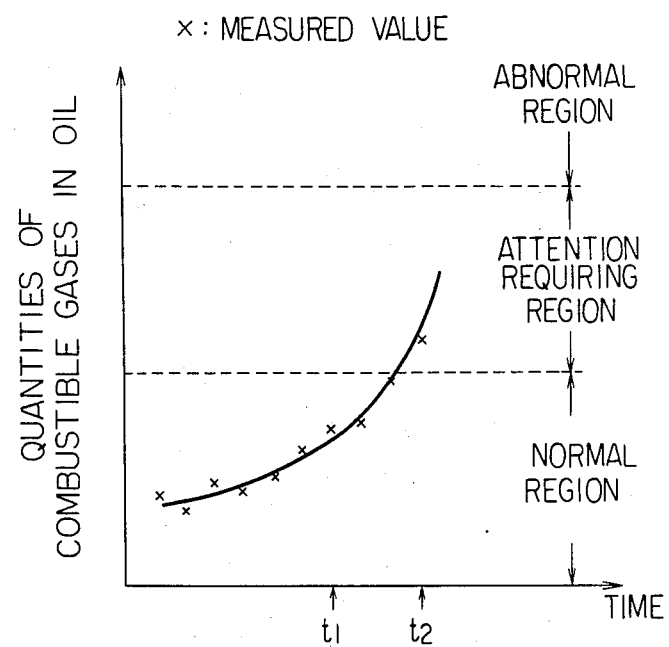
FIG. 1 is a diagram showing the characteristic curve of a variation with time in the quantities of combustible gases in oil.
Figure 2:
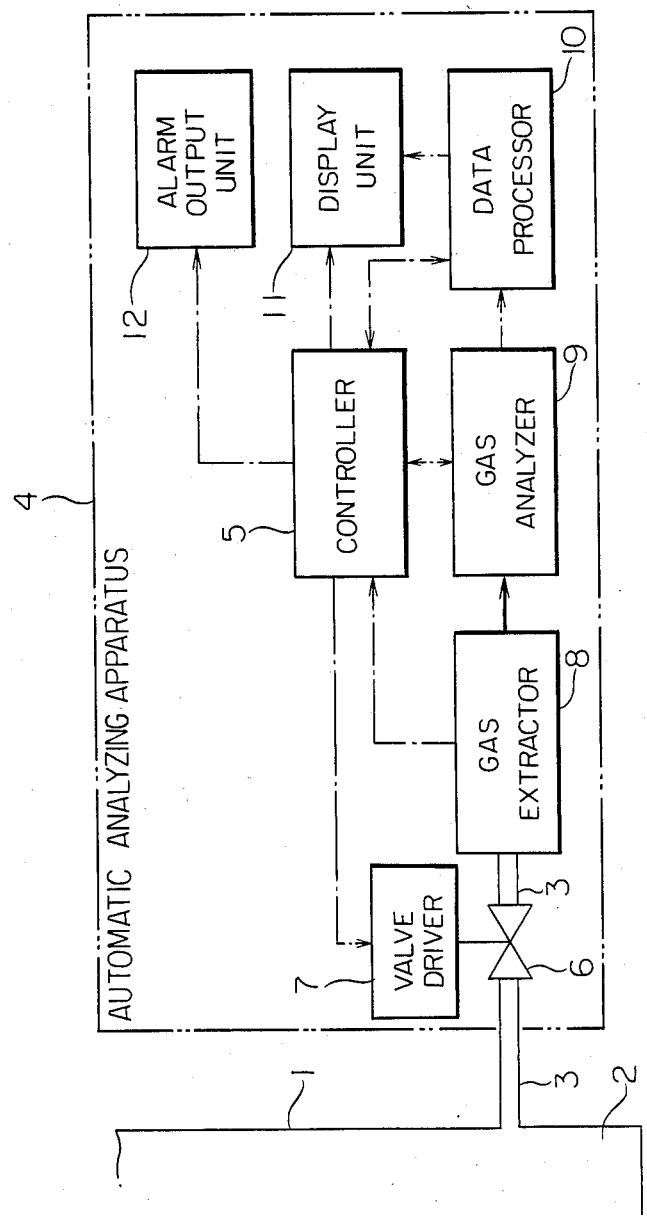
FIG. 2 is a block diagram showing an embodiment of this invention.

FIG. 2 is a block diagram showing an embodiment in which this invention is applied to an oil-immersed transformer. An oil-immersed transformer 1 contains an insulating oil 2 therein, and is coupled by an oil sampling pipe 3 with an apparatus for automatically analyzing apparatus gases in oil 4. This automatic analyzing apparatus 4 comprises a controller 5 to be described in detail later, a valve 6 disposed in the oil sampling pipe 3, a valve driver 7 opening or closing the valve 6 in accordance with the signal of the controller 5, a gas extractor 8 coupled to the oil sampling pipe 3 to derive the insulating oil 2 from the oil-immersed transformer 1 through the valve 6 and to extract combustible gases from the oil, a gas analyzer 9 for deriving the combustible gases extracted by the gas extractor 8 to detect the quantities of the combustible gases, a data processor 10 for storing data just analyzed by the gas analyzer 9, for finding a variation with time in the quantities of the combustible gases on the basis of the data in several past analyzing steps and for determining the presence or absence of the abnormality in the oil-immersed transformer 1 from an increasing or decreasing trend of the analyzed results, a display unit 11 for displaying the determined result through the data processor 10, and an alarm output unit 12. The constituent devices 7–12 have their operations controlled in a proper sequence by the controller 5. In the figure, an arrow in a solid line indicates the flow of the combustible gases, arrows in dotted lines indicate the flows of data, and arrows in dot-and-dash lines indicate the flows of control signals.

With the automatic analyzing apparatus 4 constructed as described above, the valve driver 7 is started every fixed period by the controller 5 so as to open and close the valve 6, whereby the insulating oil 2 in a predetermined amount is fed into the gas extractor through the oil sampling pipe 3. Subsequently, the gas extractor 8 extracts combustible gases from the insulating oil 2 when it has received a start signal from the controller 5, and it transmits an end signal to the controller 5 when it has sent the extracted combustible gases into the gas analyzer 9. When the gas analyzer 9 has received a gas analysis start signal from the controller 5, it measures and analyzes the total quantity of the combustible gases or the quantities of several specified ones of the combustible gases, such as $C_2H_2$ (acetylene), whereupon it transmits analytical data to the data processor 10 and outputs an end signal to the controller 5. Subsequently, when started by the controller 5, the data processor 10 finds the increasing trend or decreasing trend per certain predetermined time interval, of the analytical results of the total quantity of the combustible gases or the quantities of the several specified sorts of combustible gases on the basis of the latest data and the data of several past analyzing operations already stored. To be added is that, since the gas analytical result involves errors having developed in the gas extractor 8 and the gas analyzer 9 before the completion of the analysis, the data processor 10 executes, e.g., statistic processing routine in which the dispersion of data is considered. Further, the data processor 10 compares the increasing trend of the quantities of the combustible gases found with a preset allowable value to determine the presence or absence of an abnormality, and it outputs a calculated result to the display unit 11 and also outputs an abnormality determination signal and a processing end signal to the controller 5. The display unit 11 displays the calculated result upon receiving an output signal from the controller 5, and the alarm output portion 12 gives an alarm such as contact output upon receiving an abnormality occurrence signal from the controller 5.

Figure 3:
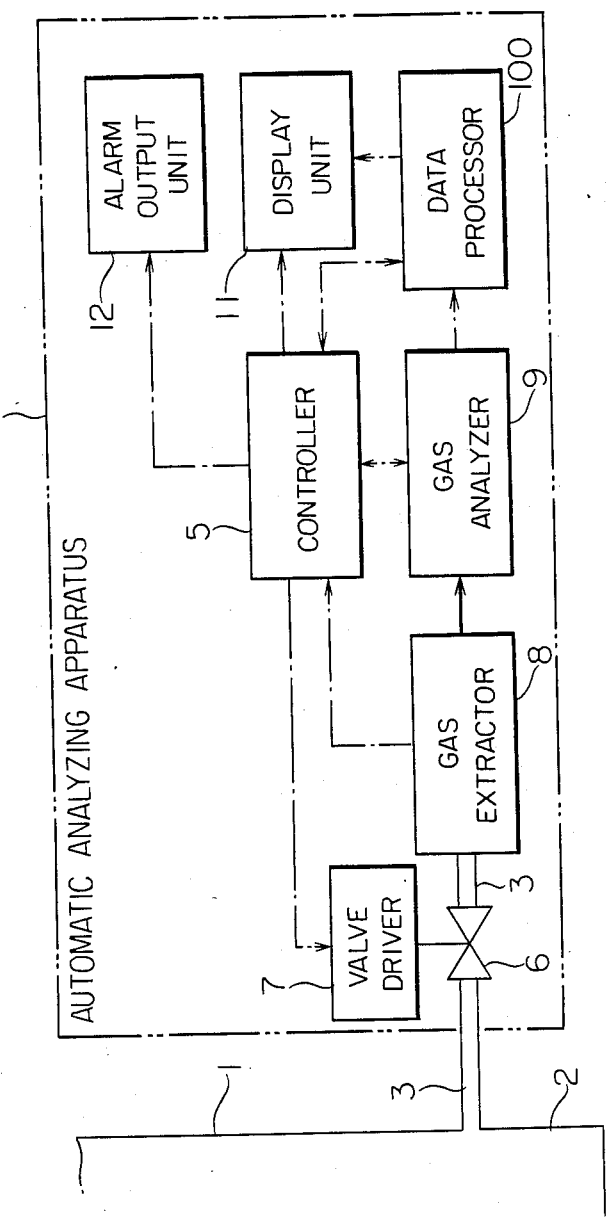
FIG. 3 is a block diagram showing another embodiment of this invention.
Figure 4:
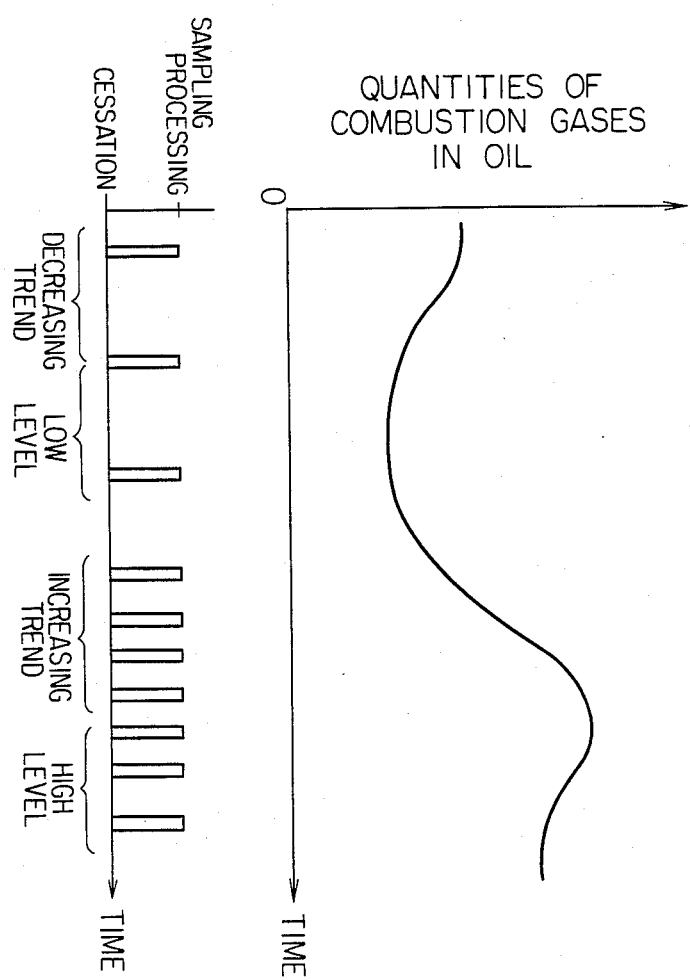
FIG. 4 is a waveform diagram showing an example of sampling times versus the variation with time of the quantities of combustible gases in oil.

FIG. 3 is a block diagram showing another embodiment of this invention. Since this embodiment differs from the foregoing embodiment of FIG. 2 in only the data processor and is identical thereto in all the other constituent components, only the former shall be described in detail. When started by the controller 5, the data processor 100 stores gas data just analyzed by the gas analyzer 9, finds the variation with time of the combustible gas quantities on the basis of the stored data and the data of the past several analyzing operations and calculates the sampling period of oil sampling and analytical processing routines on the basis of at least one of an increasing or decreasing trend of analytical results per predetermined time interval and the combustible gas quantities exceeding a predetermined level. As illustrated in FIG. 4 by way of example, a short sampling period is calculated based on an increasing trend or a high level, whereas a lone sampling period is calculated based on a decreasing trend or a low level. The data processor 100 further outputs the calculated result to the display unit 11 and outputs the calculated sampling period and a processing end signal to the controller 5. Consequently, the controller 5 starts its next operation under the revised sampling period.

In the above embodiments, the presence or absence of the abnormality, the sampling period, etc. have been determined with note taken of an increasing trend or decreasing trend of the total quantity of the combustible gases in the oil or the quantities of the several sorts of specified combustible gases. In general, however, the precision of a gas analysis is inferior in a case where the combustible gas quantities are slight. When, with this fact taken into account, the data processor is so constructed as to determine the presence or absence of the abnormality in the oil-immersed equipment, the sampling period, etc. on the basis of an increasing trend or decreasing trend of the combustible gas quantities only in case the combustible gas quantities exceed a certain predetermined value, erroneous decisions for slight quantities of the combustible gases can be prevented.

As thus far described, according to this invention, an apparatus for automatically analyzing the quantities of combustible gases dissolved in the oil of oil-immersed equipment is provided with the function of storing the combustible gas quantities, statistically processing several analytical results (combustible gas quantities) to automatically find an increasing trend or decreasing trend of the combustible gas quantities and the oil-immersed equipment from the trend, and the function of automatically changing a sampling period. These bring forth the effect that labor and skills having heretofore been required for data processing and for determining the presence or absence of a an abnormality are dispensed with, and also the effect that much labor in case of a short sampling period and expenses therefor are mitigated.

What is claimed is:
1. An apparatus for automatically analyzing gases in oil comprising:
   a gas extractor for deriving a slight amount of oil from an oil-immersed equipment to extract combustible gases contained therein in accordance with a sampling rate;
   a gas analyzer for deriving the combustible gases extracted by the gas extractor to analyze the total quantity of the combustible gases or quantities of specified combustible gases; and
   a data processor for storing results analyzed by the gas analyzer, for determining the trend of combustible gas quantities exceeding a predetermined value in the sample oil and the presence or absence of an abnormality in the oil-immersing equipment thereby, for compensating for errors in the results of the gas analyzer by performing statistical processing in which dispersion of data is considered, and for automatically adjusting the sampling rate of oil sampling and analytical processing routines on the basis of an increasing or decreasing trend of the analyzed results.

* * * * *